United States Patent [19]

Cordier et al.

[11] Patent Number: 4,973,768
[45] Date of Patent: Nov. 27, 1990

[54] PROCESS FOR THE PREPARATION OF UNSATURATED ALCOHOLS

[75] Inventors: Georges Cordier, Francheville; Pierre Fouilloux, Caluire et Cuire; Jean-Michel Grosselin, Lyons, all of France

[73] Assignee: Rhone-Poulenc Sante, Antony, France

[21] Appl. No.: 319,189

[22] Filed: Mar. 6, 1989

[30] Foreign Application Priority Data

Mar. 8, 1988 [FR] France .................................. 88 02919

[51] Int. Cl.⁵ ........................ C07C 29/14; C07C 27/04
[52] U.S. Cl. ..................................... 568/814; 568/813; 568/846; 568/862; 568/863; 568/874; 568/880
[58] Field of Search ............... 568/814, 846, 845, 862, 568/863, 874, 813, 880, 878

[56] References Cited

U.S. PATENT DOCUMENTS

| | | | |
|---|---|---|---|
| 3,953,524 | 4/1976 | Steiner | 568/814 |
| 4,298,766 | 11/1981 | Broecker et al. | 568/862 |
| 4,837,367 | 6/1989 | Gastafson et al. | 568/862 |

*Primary Examiner*—Werren B. Lone
*Attorney, Agent, or Firm*—Stevens, Davis, Miller & Mosher

[57] ABSTRACT

Unsaturated alcohols are prepared by hydrogenation of the corresponding carbonyl compounds in the presence of a platinum-cobalt bi-metallic catalyst having an alloy structure.

8 Claims, No Drawings

PROCESS FOR THE PREPARATION OF UNSATURATED ALCOHOLS

The present invention relates to the preparation of unsaturated primary and secondary alcohols by hydrogenation of the corresponding aldehydes and ketones.

From French Patent FR No. 74 09255 (Publication No. 2 234 258), it is known that $\alpha,\beta$-unsaturated alcohols may be prepared by hydrogenation of $\alpha,\beta$-unsaturated aldehydes in the presence of a catalyst consisting of previously reduced platinum oxide in combination with a cobalt salt. Although the catalyst may in theory be obtained by reducing a suspension of elementary platinum and the required quantity of cobalt salt at ambient temperature and pressure, it is clear from the examples that the reduction of the $\alpha,\beta$-ethylenic aldehydes is achieved by hydrogenating a mixture of previously reduced platinum oxide, $\alpha,\beta$-unsaturated aldehyde and cobalt salt. This catalyst quickly loses its activity and can be difficult to recycle because it is necessary to determine the relative proportions of platinum and cobalt at each recycling.

It has now been found that a bi-metallic platinum-cobalt catalyst in which the platinum and the cobalt form an alloy enables unsaturated aldehydes to be reduced to unsaturated alcohols with an increased rate of reaction and selectivity.

The present invention accordingly provides a process for the preparation of unsaturated alcohols of formula:

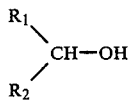

in which $R_1$ and $R_2$, which are identical or different, each represents a hydrogen atom or a saturated or unsaturated aliphatic radical, which is unsubstituted or substituted by a saturated or unsaturated alicyclic or aromatic radical, or $R_1$ and $R_2$ together form an unsaturated alicyclic radical, provided that:

$R_1$ and $R_2$ do not both represent hydrogen, and
at least one of $R_1$ and $R_2$ contains an ethylenic double bond,
the said aliphatic, alicyclic or aromatic radicals being unsubstituted or substituted by one or more identical or different substituent radicals selected from alkyl of 1 to 4 carbon atoms, hydroxy and alkoxy of 1 to 4 carbon atoms, which comprises hydrogenating a carbonyl compound of formula:

in which $R_1$ and $R_2$ are as defined above, in the presence of a bi-metallic platinum-cobalt catalyst having an alloy structure on a support.

The new process is especially suitable for the preparation of $\alpha,\beta$-unsaturated alcohols from the corresponding $\alpha,\beta$-unsaturated carbonyl compounds, that is to say the preparation of products of formula (I) in which one at least of the symbols $R_1$ and $R_2$ contains a double bond in the $\alpha,\beta$-position relative to the alcohol function from the corresponding $\alpha,\beta$-unsaturated compounds of formula (II).

More particularly, the present invention provides a process for the preparation of $\alpha,\beta$-unsaturated alcohols of formula (I) in which one of symbols $R_1$ and $R_2$ represents a hydrogen atom and the other represents an aliphatic radical of 1 to 30 carbon atoms and at least one double bond in the $\alpha,\beta$-position relative to the alcohol function, which is unsubstituted or substituted by one or more identical or different radicals selected from alkyl of 1 to 4 carbon atoms, hydroxy, alkoxy of 1 to 4 carbon atoms, saturated and unsaturated alicyclic radicals of 5 or 6 carbon atoms which are unsubstituted or substituted by one or more alkyls of 1 to 4 carbon atoms each, and unsubstituted or substituted phenyl, or $R_1$ and $R_2$ together form an unsaturated alicyclic radical which is unsubstituted or substituted by one or more alkyls of 1 to 4 carbon atoms each, from the corresponding $\alpha,\beta$-unsaturated carbonyl compounds of general formula (II).

The process may especially advantageously be applied to the preparation of prenol from prenal, of nerol/geraniol from citral, of crotyl alcohol from crotonaldehyde or cinnamic alcohol from cinnamaldehyde.

The new catalysts, which constitute another subject of the present invention, are of bi-metallic type (Pt+Co) deposited on a support of high specific surface area. Generally, the support is charcoal having a specific surface area greater than 1000 m²/g, and preferably close to 1500 m²/g.

Generally, the catalysts of the invention are prepared by bringing the support, preferably charcoal, into contact with a solution of a platinum derivative and an inorganic or organic cobalt salt in quantities such that:
  the Pt/Co ratio (gram-atom/gram-atom) is between 1/9 and 9/1 and
  the sum of the weights of the two metals deposited on the support represents 1 to 10% by weight relative to the weight of the support, and preferably 3 to 5%.

After evaporation of the solvent at moderate temperature below 120° C., the impregnated support is heated in a stream of hydrogen to a temperature between 400° and 500° C. for 4 to 8 hours.

After cooling, the reduced catalyst thus obtained is ready for use.

Generally the solvent used for impregnating the support is an aromatic hydrocarbon (e.g. benzene or toluene) containing 1 to 5% of an aliphatic alcohol of 1 to 4 carbon atoms (e.g. methanol or ethanol).

The platinum derivative is, preferably, chloroplatinic acid ($H_2PtCl_6$) but other derivatives such as platinum nitrate or acetylacetonate, $Pt(NH_3)_4Cl_2$ or $Pt(NH_3)_4(OH)_2$ give satisfactory results.

The cobalt salt may be an inorganic salt (e.g. cobalt nitrate) or an organic salt (e.g. cobalt acetate or cobalt acetylacetonate).

It is particularly advantageous to use a support that contains no iron. To ensure this, prior to impregnation, the support may be washed with a boiling aqueous solution of an acid, such as 2N hydrochloric acid, and then with water so as to eliminate the anion originating from the acid used in the washing process. The support, thus washed, is then treated at high temperature (e.g. 400° C.) in an inert atmosphere (e.g. nitrogen), prior to impregnation.

In the catalysts according to the present invention the Pt/Co ratio (gram-atom/gram-atom) may vary between 1/9 and 9/1.

Generally, examination of a catalyst of the invention by electron microscopy (T.E.M.) shows the presence of small particles (30–40 Å) and of larger clusters (80–120 Å) resulting from the agglomeration of the smaller particles. Moreover, examination with a STEM beam of 10 Å diameter shows that all the grains are bi-metallic (Pt +Co) and that, generally, the concentration of cobalt is higher on the outside of the particles than inside them.

The selective hydrogenation of unsaturated aldehydes of formula (II) to unsaturated alcohols of formula (I) is usually carried out at a temperature between 0 ⓡ and 160° C., preferably between 30° and 80° C., operating in an organic solvent. The operating pressure is generally between 1 and 200 bars, and preferably between 5 and 50 bars.

The organic solvent is preferably a polar solvent which is an alcohol (e.g. methanol, ethanol or isopropanol) optionally in combination with an aliphatic (e.g. pentane, hexane, heptane or octane), alicyclic (e.g. cyclohexane), or aromatic (e.g. benzene, toluene or xylene) hydrocarbon, an ether (e.g. diethyl or diisopropyl ether) or an ester (e.g. methyl acetate, ethyl acetate or butyl acetate).

It is advantageous to add a quantity of water to the polar solvent or mixtures of solvents up to 35% of the total volume in a manner such that the medium remains homogeneous.

Generally, 0.1 to 5% of the weight of catalyst is used relative to the unsaturated aldehyde or ketone starting material.

The process of the invention enables unsaturated alcohols of formula (I) to be obtained with a selectivity generally above 85%.

The following Examples illustrate the invention.

EXAMPLE 1 - Catalyst preparation

A solution in benzene (100 cc, containing 3% by volume of ethanol) of chloroplatinic acid ($H_2PtCl_6$) and hydrated cobalt nitrate [$Co(No_3)_2 \cdot 6H_2O$] in quantities such that the Pt/Co ratio (gram-atom/gram-atom) is 1/9, 2/8, 3/7, 4/6, 5/5, 6/4, 7/3, 8/2, and 9/1 and the sum of the weights of the two metals is 5% of the weight of charcoal, is added to charcoal (10 g) having a specific surface area of 1400 $m^2/g$ which has previously been washed with boiling 2N hydrochloric acid and with water to eliminate the chloride ions, and then calcined at 400° C. under nitrogen for 1 hour. The solvent is evaporated with stirring and under reduced pressure (100 mm Hg; 13.3 kPa).

The charcoal thus impregnated is heated to 120° C. for 15 hours under a stream of helium. It is then cooled before being heated to 450° C. at a rate of 2° C. per minute, under a stream of hydrogen. It is maintained at 450° C. for 6 hours.

After cooling, the catalysts thus obtained are ready for use.

EXAMPLES 2 TO 10

Isopropanol (40 cc), an aqueous solution of sodium acetate (0.1 mole/liter, 2 cc) and a catalyst prepared in Example 1 (0.3 g) are placed in a 150-cc autoclave agitated by a turbine ensuring good liquid-gas transfer. The autoclave is purged three times with nitrogen under pressure (5 bars), and then three times with hydrogen under pressure (5 bars). Cinnamic aldehyde (0.1 mole) is added. Agitation is begun and the hydrogen pressure is raised to 40 bars. The contents of the autoclave are heated to 60° C. The pressure is maintained constant throughout the hydrogenation, whose course is monitored by the consumption of hydrogen and analysis of the reaction mixture by gas phase chromatography.

The results obtained are shown in Table 1.

TABLE

| Example | Pt/Co ratio (g-at/g-at) | Rate of conversion of cinnamic aldehyde % | Yield of cinnamic alcohol % | Rate of hydrogenation mole $H_2/h/g$ of Pt |
|---|---|---|---|---|
| 2 | 1/9 | 88.2 | 75.1 | 0.011 |
| 3 | 2/8 | 89.7 | 80.3 | 0.025 |
| 4 | 3/7 | 92.1 | 86.5 | 0.026 |
| 5 | 4/6 | 93.1 | 89.2 | 0.032 |
| 6 | 5/5 | 94.9 | 90.0 | 0.108 |
| 7 | 6/4 | 94.7 | 91.0 | 0.098 |
| 8 | 7/3 | 93.7 | 93.5 | 0.092 |
| 9 | 8/2 | 89.3 | 88.1 | 0.086 |
| 10 | 9/1 | 88.6 | 67.5 | 0.080 |

EXAMPLE 11 (Comparative example)

Charcoal having a specific surface area of 1400 $m^2/g$ is impregnated with a solution of chloroplatinic acid in benzene containing 3% of ethanol in a manner such that the quantity of platinum deposited represents 5% weight of the charcoal.

After evaporation of the solvent, the impregnated charcoal is heated to 450° C. for 6 hours under a stream of hydrogen.

Isopropanol (40 cc), an aqueous solution of sodium acetate (0.1 mole/liter) (2 cc) and the catalyst (Pt/charcoal 5 %) (0.3 g) are placed in a 150-cc autoclave.

Cinnamic aldehyde (0.1 mole) and cobalt salt ($Co(NO_3)_2 6H_2O$) are added in a manner such that the Pt/Co ratio is equal to 6/4 (gram-atom/gram-atom).

The pressure of hydrogen is established at 40 bars and the mixture heated to 60° C.

The progress of the reaction is followed by gas phase chromatography.

The results obtained are as follows:
the rate of conversion of cinnamic aldehyde is 98.9%,
the yield of cinnamic alcohol is 88%,
the rate of hydrogenation is 0.0065 mole of hydrogen/hour/g of platinum.

Comparison of this example with, in particular, Examples 6 and 7 shows that a catalyst according to the invention enables better selectivity to be obtained with a distinctly higher rate of hydrogenation.

EXAMPLES 12 AND 13

Catalyst (prepared as described in Example 1, 0.3% by weight relative to prenal) and isopropanol containing 5% of water (10 cc) are successively introduced into a 125-cc stainless-steel autoclave. The heterogeneous mixture is placed under hydrogen pressure of 30 bars at 70° C. for 16 hours. Then prenal ($17 \times 10^{-3}$ mole, 1.43 g) is added. The reaction mixture is hydrogenated at 55° C. under a hydrogen pressure of 30 bars.

The results obtained are shown in Table 2.

TABLE 2

| Example | Pt/Co ratio (g-at./g-at.) | Duration of hydrogenation | Rate of conversion of prenal % | Selectivity for prenol % |
| --- | --- | --- | --- | --- |
| 12 | 8/2 | 5 hours 40 | 58 | 88 |
| 13 | 3/7 | 3 hours 05 | 31.5 | 88 |

We claim:

1. Process for the preparation of an unsaturated alcohol of formula:

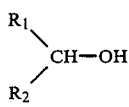

in which $R_1$ and $R_2$, which are identical or different, each represents a hydrogen atom or a saturated or unsaturated aliphatic radical, which is unsubstituted or substituted by a saturated or unsaturated alicyclic or aromatic radical, or $R_1$ or $R_2$ together form an unsaturated alicyclic radical, provided that $R_1$ and $R_2$ do not both represent hydrogen and at least one of $R_1$ and $R_2$ contains an ethylenic double bond, the said aliphatic, alicyclic or aromatic radicals being unsubstituted or substituted by one or more identical or different substituent radicals selected from alkyl of 1 to 4 carbon atoms, hydroxy, and alkoxy of 1 to 4 carbon atoms which comprises hydrogenating with gaseous hydrogen at a pressure between 1 and 200 bars and at a temperature between 0 and 160° C. a carbonyl compound of formula:

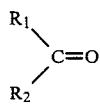

in which $R_1$ and $R_2$ are as defined above, in the presence of a bi-metallic platinum-cobalt catalyst having an alloy structure, on a support.

2. Process according to claim 1 in which, in the bi-metallic catalyst, the Pt/Co ratio, expressed in gram-atom/gram-atom, is between 1/9 and 9/1.

3. Process according to claim 1 in which the support is iron-free charcoal having a specific surface area greater than 1000 m²/g.

4. Process according to claim 1 in which the sum of the weights of the two metals represents 1 to 10% of the weight of the support.

5. Process according to claim 1 in which the process is carried out in an organic polar solvent which is an alcohol, alone or in combination with a non-polar aliphatic, cycloaliphatic or aromatic hydrocarbon, an ether or an ester.

6. Process according to claim 5 in which the solvent or solvent mixture contains up to 35% of the total volume of water.

7. Process according to claim 1 in which a carbonyl compound of the said formula in which one of the radicals $R_1$ and $R_2$ represents a hydrogen atom and the other represents an aliphatic radical of 1 to 30 carbon atoms and at least one double bond in the $\alpha,\beta$-position relative to the alcohol function, which is unsubstituted or substituted by one or more identical or different radicals selected from alkyl of 1 to 4 carbon atoms, hydroxy, alkoxy of 1 to 4 carbon atoms, saturated and unsaturated alicyclic radicals of 5 to 6 carbon atoms which are unsubstituted or substituted by one or more alkyls of 1 to 4 carbon atoms each, and unsubstituted or substituted phenyl, or $R_1$ and $R_2$ together form an unsaturated alicyclic radical which is unsubstituted or substituted by one or more alkyls of 1 to 4 carbon atoms, is hydrogenated.

8. Process according to claim 1 in which prenal, citral, crotonaldehyde or cinnamaldehyde is selectively hydrogenated to prenol, nerol/geraniol, crotyl alcohol, or cinnamic alcohol respectively.

* * * * *